United States Patent [19]

Carduck et al.

[11] Patent Number: 5,076,896
[45] Date of Patent: Dec. 31, 1991

[54] PROCESS FOR THE SEPARATION OF PROPYLENE GLYCOL FROM FATTY ALCOHOLS

[75] Inventors: Franz-Josef Carduck, Haan; Lutz Jeromin, Hilden; Gerd Geobel, Cologne; Wilhelm Johannisbauer; Georg Fieg, both of Erkrath; Theo Fleckenstein, Hilden, all of Fed. Rep. of Germany

[73] Assignee: Henkel Kommanditgesellschaft auf Aktien, Duesseldorf, Fed. Rep. of Germany

[21] Appl. No.: 365,577

[22] Filed: Jun. 13, 1989

[30] Foreign Application Priority Data

Jun. 13, 1988 [DE] Fed. Rep. of Germany ....... 3820040

[51] Int. Cl.$^5$ .................... B01D 3/14; B01D 11/04; C07C 31/20
[52] U.S. Cl. ...................................... 203/41; 203/18; 203/46; 203/81; 203/DIG. 19; 568/864; 568/868; 568/872; 568/913
[58] Field of Search ....................... 203/41, 43, 46, 18, 203/81, DIG. 19, 99; 568/868, 872, 913, 864, 861

[56] References Cited

U.S. PATENT DOCUMENTS

| | | | |
|---|---|---|---|
| 2,629,686 | 2/1953 | Grosser | 568/868 |
| 3,574,772 | 4/1971 | Becker et al. | 568/868 |
| 3,816,549 | 6/1974 | Prinz | 568/868 |

FOREIGN PATENT DOCUMENTS

| | | | |
|---|---|---|---|
| 254189 | 1/1988 | European Pat. Off. | |
| 218613A1 | 2/1985 | Fed. Rep. of Germany | |
| 3432719 | 3/1986 | Fed. Rep. of Germany | 568/868 |
| 54-12304 | 1/1979 | Japan | 568/868 |
| 55-20749 | 2/1980 | Japan | 568/868 |

OTHER PUBLICATIONS

R. K. Freier, "Aqueous Solutions", vol. 1, pp. 280 and 346, (1976).
Ullmans Encyklopaedie der technischen Chemie, vol. 2, (1972), pp. 562–563, 568, 570.

Primary Examiner—Wilbur Bascomb
Attorney, Agent, or Firm—Ernest G. Szoke; Wayne C. Jaeschke; John E. Drach

[57] ABSTRACT

A process for the separation of propylene glycol from a mixture of low-boiling fatty alcohols and propylene glycol which comprises extracting the mixture with water to produce a water-propylene glycol mixture and fractionating the water-propylene glycol mixture to produce propylene glycol that is substantially anhydrous and an apparatus for carrying out the process.

9 Claims, 1 Drawing Sheet

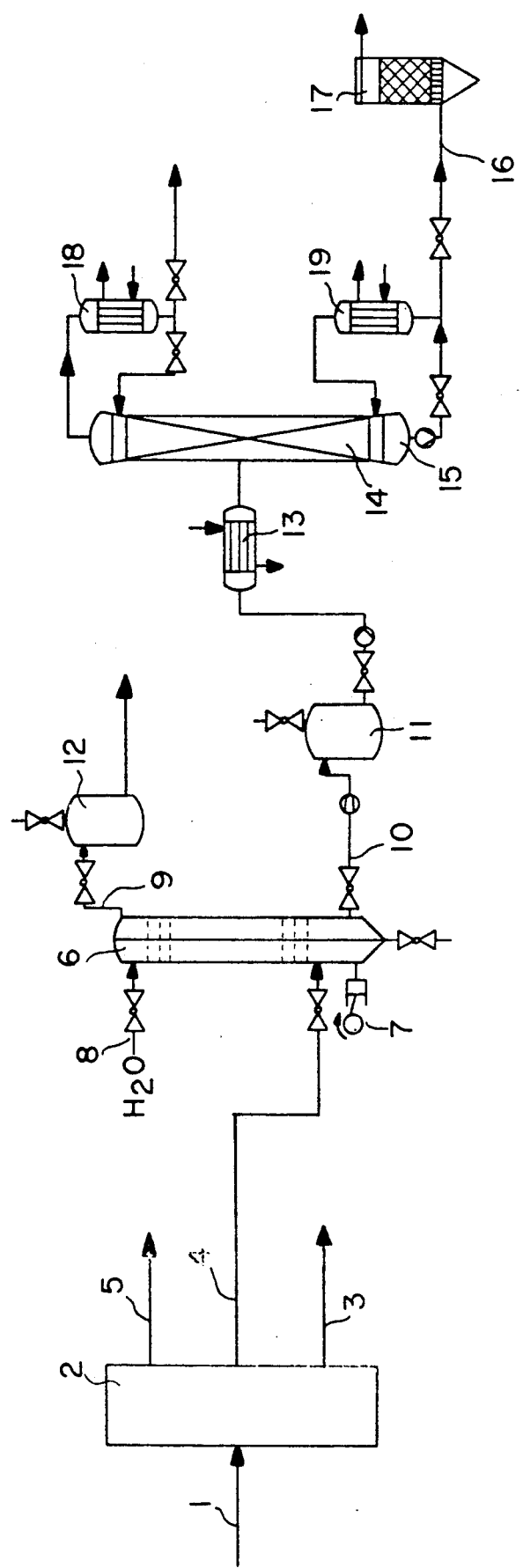

PROCESS FOR THE SEPARATION OF PROPYLENE GLYCOL FROM FATTY ALCOHOLS

BACKGROUND OF THE INVENTION

1. Field of the Invention

This invention relates to a process for the separation of propylene glycol from a mixture of low-boiling fatty alcohols and propylene glycol. The invention also relates to an apparatus for carrying out this process.

2. Description of the Related Art

The term "low-boiling fatty alcohols" applies to fatty alcohols of which the boiling points are close to the boiling point of propylene glycol. Because of this property, the propylene glycol cannot be separated by rectification.

The problem addressed by the invention is to provide a process for the separation of propylene glycol from a mixture of low-boiling fatty alcohols and propylene glycol which is economical and provides for the substantially complete removal of propylene glycol from fatty alcohols. A solution to this problem was only found after extensive tests.

SUMMARY OF THE INVENTION

According to the invention, a process for separating propylene glycol from a mixture of low-boiling fatty alcohols and propylene glycol is provided comprising the steps of: (a) extracting the mixture with water to produce a water-propylene glycol mixture and a water-fatty alcohol acid mixture; (b) fractionating the water-propylene glycol mixture to produce a distillate that contains at least about 95% by weight propylene glycol.

This process can be accomplished by means of an apparatus comprising (a) an extraction column having a first inlet means at the top portion of said column for receiving water; (b) a second inlet means at the bottom portion of said column for receiving a hydrogenation effluent first cut connected to the outlet of a rectification column; (c) an outlet means at the bottom portion of said extraction column for removing a water-propylene glycol mixture extract; (d) a heat exchanger means for heating said water-propylene glycol mixture extract having an inlet means for receiving said water-propylene glycol mixture extract connected to said outlet means at the bottom of said extracting column, and having an outlet means for removing heated water-propylene glycol mixture extract; (e) a fractionating column having an inlet means connected to said outlet means of said heat exchanger means and an outlet means at the bottom of said fractionating column for removing substantially anhydrous propylene glycol.

BRIEF DESCRIPTION OF THE DRAWING

FIG. 1 shows a flow diagram for the separation of propylene glycol from a mixture of low-boiling fatty alcohols and propylene glycol.

DESCRIPTION OF THE PREFERRED EMBODIMENTS

The present invention provides a process for producing substantially anhydrous propylene glycol from a mixture of low-boiling fatty alcohols and propylene glycol which is obtained from the first cut from the fractionation of the product stream from the direct hydrogenation of glyceride oils. The low-boiling fatty alcohols and propylene glycol mixture is first extracted with water to produce a water-propylene glycol mixture and a water-fatty alcohol mixture. In accordance with the invention, substantially anhydrous propylene glycol is produced from the water-propylene glycol extract by rectification. By virtue of very favorable equilibrium data in the water-propylene glycol system, three to five theoretical stages or plates of a rectification column are sufficient to obtain from the extract a product which—starting from an extract of 35 to 45% by weight propylene glycol and 55 to 65% by weight water—contains 97 to 99% by weight propylene glycol.

Accordingly, for the apparatus for the production of substantially anhydrous propylene glycol from a fatty alcohol/propylene glycol mixture, it is proposed in accordance with the invention that this apparatus comprise at least one extraction column and at least one following rectification column connected thereto.

The process and the apparatus according to the invention are used in particular in the working up of the reaction mixture formed in the direct hydrogenation of glyceride oils. For purposes of this invention, the reaction mixture formed in the direct hydrogenation of glyceride oils is defined as the hydrogenation effluent. For hydrogenation conversions of 97 to 99%, this reaction mixture predominantly contains fatty alcohols commensurate with the C-chain distribution of the glyceride oil used and propylene glycol commensurate with the proportion of bound glycerol and also low-boiling fractions. The object of a working-up process in this regard is to produce anhydrous propylene glycol and fatty alcohols free from propylene glycol. Tests have shown that it is of particular advantage in this case initially to fractionate the reaction mixture so that propylene glycol and low-boiling fatty alcohols are separated off as a first cut.

The hydrogenation effluent is fractionated into the following boiling cuts:
I. water/low-boiling fractions
II. first cut: $C_6/C_{10}$ fatty alcohols and propylene glycol
III. main fraction $C_{12}/C_{18}$ fatty alcohols. Analysis of a sample of the main fraction reveals $C_{12}/C_{18}$ fatty alcohols according to specification which are eminently suitable, for example, for sulfatization. This does not apply to the first cut which has to be further worked up on account of the propylene glycol therein. The hydrogenation effluent first cut contains $C_6/C_{10}$ fatty alcohols and propylene glycol. The extraction-based working up mentioned above is proposed for this purpose. Although extraction of the entire fatty alcohol after the separation of water/low-boiling fractions is possible in theory, it is disadvantageous on economic grounds.

To ensure a high concentration of propylene glycol in the extract and, hence, to achieve low further processing costs, for example in the production of substantially anhydrous propylene glycol, it is proposed that extraction of the propylene glycol take place in apparatus comprising several theoretical separation stages. It is also of advantage to carry out extraction of the propylene glycol/water mixture continuously, particularly in countercurrent manner.

Extraction is carried out particularly effectively in at least one sieve-plate extraction column. It is particularly preferred that the extraction column contain a plurality of reciprocating sieve plates.

It is also of advantage to use at least one pulsed extraction column for extraction. A pulsed extraction column is also known as a reciprocating plate column.

A reciprocating plate column provides for intimate mixing of the extractant and the liquid to be extracted by repeatedly forcing the two liquids together by mechanical agitation.

To obtain propylene glycol of high quality in regard to color, odor and composition, the substantially anhydrous propylene glycol obtained from the rectification step can be further treated with active carbon or optionally distilled overhead in another column. In the latter case, a purity of 99.69%, an acid value AV below 0.01, a saponification value SV of 0.15 and a water content of 0.16% are obtained.

In the apparatus according to the invention, the extraction column advantageously comprises several stages.

In a particularly economical embodiment, the extraction column comprises fittings, more particularly sieve plates.

In addition, the extraction column is advantageously a pulsed column.

In one particularly advantageous embodiment, the apparatus according to the invention comprises at least one other rectification column which is connected at its first cut exit to the entrance of the extraction column. With this other rectification column, it is possible for example to fractionate the hydrogenation effluent into water and low-boiling fractions, the first cut and the main fraction so that only the first cut is further processed in the remaining part of the apparatus according to the invention.

One example of embodiment of the invention is described in detail in the following with reference to FIG. 1.

FIG. 1 is a flow chart of an apparatus according to the invention for working up the hydrogenation effluent from the direct hydrogenation of glyceride oils.

Gas chromatographic analysis of a typical hydrogenation effluent produced the following values: 84% by weight fatty alcohols, 0.2% by weight hydrocarbons, 10.5% by weight propylene glycol, 1% by weight i- and n-propanol and 2.8% by weight water and traces of methanol and ethanol.

The overall process for working up the hydrogenation effluent consists of three steps, namely:
1. fractionation of the hydrogenation effluent,
2. extraction of the propylene glycol from the first cut of fractionation in the extraction apparatus,
3. rectification of the extract from the extraction apparatus and subsequent treatment of the product with active carbon.

Referring to FIG. 1, the hydrogenation effluent (1) is fractionated into three boiling cuts in a rectification column (2). The proportions by weight of the three fractions are correspondingly 5%, 22% and 73%. Analysis of the main fraction (3) produces the following values: $C_{10}$: 0.8%, $C_{12}$: 51%, $C_{14}$:21.7%, $C_{16}$: 11.2%, $C_{18}$: 14.9%, $C_{20}$: 0.1%, hydrocarbons: 0.04%, water: 0.06%. Water and low-boiling fractions are separated off at (5) at the head of the column. The first cut (4) (fatty alcohols/propylene glycol) is extracted in a pulsating (or reciprocating) sieve-plate extraction column (6). The extraction column consists of 40 sieve plates (free cross-section 14%) at intervals of 100 mm. The nominal width of the column was 100 mm. The pulsation unit (7) operates with a pulsation (reciporication) stroke of 15 mm and at a pulsation frequency of 1.5 to 1.6 l/s.

The first cut (4) is delivered to the lower part and the extractant (8), water, to the upper part of the column (6). The throughputs of the two phases are as follows: first cut: 90 to 100 $dm^3/h$, water: 40 to 50 $dm^3/h$, water being selected as the continuous phase on the basis of extensive preliminary tests. Colourless liquids are obtained as the raffinate (9) and extract (10). The raffinate (9) contains 95 to 97% by weight fatty alcohols, 3 to 4% by weight water and no propylene glycol.

The extract (10) consists of 35 to 45% by weight propylene glycol, 55 to 65% by weight water and traces of the above-mentioned low-boiling fractions.

The raffinate (9) is collected in the vessel (12). The extract from the vessel (11) is brought to the operating temperature (approx. 100° C.) in the heat exchanger (13) and delivered to the rectification column (14). A packed rectification column (Kühni Rombopack, height: 4 m, diameter: 316 mm) operated at normal pressure (1 bar) with a reflux ratio of 0.5 is used. The extract throughput is approximately 70 kg/h which—for the reflux ratio of 0.5 mentioned above—necessitated an energy input in the evaporator (19) of the column of approximately 40 to 47 kW. The throughputs of the two head and sump products amounts correspondingly to 42 kg/h and 28 kg/h. The slight yellowish coloration of the sump product (16) (97 to 99% by weight propylene glycol) and its faint odor can be completely removed without difficulty by subsequent treatment (17) with active carbon (for example NORJT CA1 or BRILLONIT; active carbon consumption: approx. 1 to 2 g/100 g). The drawing also shows the column sump at (15) and a condenser at (18).

What is claimed is:

1. A process for separating propylene glycol from a mixture of $C_6/C_{10}$ low-boiling fatty alcohols and propylene glycol comprising the steps of: (a) extracting said mixture with water to produce a water-propylene glycol mixture and a water-fatty alcohol mixture; and (b) fractionating said water-propylene glycol mixture to produce a distillate that contains at least about 95% by weight propylene glycol.

2. The process of claim 1 wherein said mixture of low-boiling fatty alcohols and propylene glycol is a first cut from the fractionation of a hydrogenation effluent from the direct hydrogenation of glyceride oils.

3. The process of claim 1 wherein said distillate from step (b) is distilled to produce a second distillate that contains at least 99% by weight propylene glycol.

4. The process of claim 1 further comprising the step of treating the distillate from step (b) with activated carbon for a sufficient time to remove color and odor from said distillate.

5. The process of claim 1 wherein step (a) is carried out continuously.

6. The process of claim 5 wherein step (a) is carried out counter-currently.

7. The process of claim 1 wherein step (a) the water-propylene glycol mixture contains from about 35% to about 45% by weight of propylene glycol and from about 55% to about 65% by weight of water.

8. The process of claim 1 wherein in step (b) the distillate contains from about 97 % to about 99% by weight of propylene glycol.

9. The process of claim 1 wherein step (a) is carried out continuously and counter-currently and the water-propylene glycol mixture contains from about 35% to about 45% by weight of propylene glycol and from about 55% to about 65% by weight of water, and wherein step (b) the distillate contains from about 97% to about 99% by weight of propylene glycol.

* * * * *